United States Patent
Mallow

[11] Patent Number: 5,945,558
[45] Date of Patent: *Aug. 31, 1999

[54] METHOD OF MAKING AMINO ACID ACRYLIC MONOESTERS

[75] Inventor: William A. Mallow, Helotes, Tex.

[73] Assignee: Southwest Research Institute, San Antonio, Tex.

[*] Notice: This patent is subject to a terminal disclaimer.

[21] Appl. No.: 08/886,705

[22] Filed: Jul. 1, 1997

Related U.S. Application Data

[63] Continuation-in-part of application No. 08/683,321, Jul. 18, 1996, Pat. No. 5,810,595.

[51] Int. Cl.⁶ ...................... C07C 229/30; C07D 513/04; A61C 5/04; A61C 5/08
[52] U.S. Cl. .......................... 560/172; 560/155; 548/227; 433/226; 433/228.1; 433/217.1; 433/222.1
[58] Field of Search ..................................... 560/155, 172; 548/227; 433/226, 228.1, 217.1, 222.1

[56] References Cited

U.S. PATENT DOCUMENTS

| | | |
|---|---|---|
| 3,785,832 | 1/1974 | Bowen . |
| 4,051,302 | 9/1977 | Mayama et al. . |
| 4,069,214 | 1/1978 | Onizawa . |
| 4,102,856 | 7/1978 | Lee, Jr. . |
| 4,514,527 | 4/1985 | Bowen . |
| 4,588,756 | 5/1986 | Bowen . |
| 4,659,751 | 4/1987 | Bowen . |
| 4,964,911 | 10/1990 | Ibsen et al. . |
| 5,133,957 | 7/1992 | Suh et al. . |

OTHER PUBLICATIONS

Project No. 5 P50 DE09307–07, Soderholm, Karl–Johan M. "Conditioning and Bonding Agents for Resin Based Composites." 1995.
Project No. 7 RO 3 DE10794–02, Kao, Elizabeth C. "Improved Amino Acid–Modified Dental Glass Ionomers", 1994.
Project No. 5 RO1 DE10177–03, Marshall, Sally J. "Development of EDTA–Derivative Dentin Bonding Systems" 1994.
Database Caplus on STN, Acc No. 1991:102741, Belshaw et al., Chlorotrimethylsilane mediated formation of .omega.–allyl esters of aspartic and glutamic acids.' Synth. Comm. (1990), 20(20), pp. 3157–3160, abstract, 1990.

*Primary Examiner*—Brian M. Burn
*Assistant Examiner*—Brian J. Davis
*Attorney, Agent, or Firm*—John L. Sigalos

[57] ABSTRACT

A method is disclosed for making dibasic amino acid monoesters useful in repair of teeth in which a dibasic amino acid is partially esterified with an allylic acrylic compound in the presence of an acidic ion-exchange resin at ambient temperature. The invention also comprises cyclicizing the amino groups of the monoesters.

20 Claims, No Drawings

METHOD OF MAKING AMINO ACID ACRYLIC MONOESTERS

CROSS-REFERENCE TO RELATED APPLICATION

The instant invention is a continuation-in-part of application Ser. No. 08/683,321 filed Jul. 18, 1996, now U.S. Pat. No. 5,810,595.

BACKGROUND OF THE INVENTION

The instant invention relates to the method of making amino acid acrylic monomers, particularly for use in compositions suitable for dental repair; i.e., a dental filling for dental adhesive.

There have been repeated efforts to replace amalgam as a filling in dental practice, as well as to have suitable adhesives for dental purposes other than for fillings. One polymeric material that has been suggested for such use is bis-glycidylmethylmethacrylate polymer (bis-GMA). When used as a dental adhesive or filling, together with the other usual components admixed therewith, such bis-GMA offers good mechanical and physical properties, but exhibits considerable post-shrinkage and relative poor adhesion to bone substrate. Thus, it is not entirely satisfactory for use as an adhesive in dental work or as a filling. The use of such GMA material is disclosed in U.S. Pat. Nos. 4,588,756 and 4,964,911.

U.S. Pat. No. 4,659,751 discusses the use of a variety of acids and other materials in order to treat the surface of teeth, such as enamel and dentin, to activate the surfaces for improved adhesion to polymers, but no disclosure or suggestion is made therein of the use of the GMA or bis-GMA.

In this regard, it is well known that in order to achieve desired bonding on enamel or dentin, the protein coatings on the enamel and the smear level on dentin must be removed. Traditionally, this has been done utilizing organic acids such as phosphoric, citric, and lactic acids, as well as ethylene diamine dicarboxylic acid. Accordingly, many of the new products provide such polyacids as surface cleaning and priming agents for enamel and dentin. At the present time bis-GMA resins themselves are not inherently adhesive to tooth surfaces, and if used acid etching is required.

Dibasic amino acids partially esterified with allyl alcohol or a hydroxyalkyl acrylate or methacrylate and cyclized have been found to overcome the problems associated with bis-GMA and such are disclosed in detail in the parent application identified above whose entire disclosure is specifically incorporated herein by reference.

However, it has been found that the method of making such partially esterified materials is material intensive, time consuming, and most importantly require such high acid strength that it often resulted in complete esterification leaving little or no functionality for adhesion to dentin. Moreover, the amino group remaining in the structure were so sterically hindered by the large acrylate or methacrylate moiety at each end, that it was difficult to formulate the esters as adhesive primers for dental use.

SUMMARY OF THE INVENTION

The present invention overcomes the problems of the prior art and provides a method for making partial esters in excellent yield and which can be easily recovered.

Briefly stated, the present invention comprises a method of making monomers of dibasic amino acids by condensing them with a hydroxyl functional acrylic compound at ambient temperature in the presence of an acidic ion-exchange resin.

The invention also comprises cyclicizing such monoesters.

DETAILED DESCRIPTION

As used herein, the term "hydroxyl functional acrylic compound" refers to any hydroxy $C_1$ to $C_4$ allyl acrylate or methacrylate. Examples are 2-hydroxyethyl methacrylate (HEMA), 2-hydroxyethyl acrylate (HEA), 2-hydroxypropyl acrylate (HPA), hydroxypropyl methacrylate (HPMA), allyl alcohol and the like. The invention will be describe in connection with HEMA which is preferred.

As used herein the term "bis-GAA" refers to bis-glycidylalkylacrylate polymers in which the alkylacrylate is a $C_1$ or $C_{12}$ acrylate or methacrylate. Particularly useful are bis-glycidylmethylmethacrylate, bis-glycidylethylmethacrylate, bis-glycidylmethylacrylate, bis-ethylacrylate and mixtures thereof.

As to the dibasic amino acids used in the esterification, those utilized are glutamic and aspartic acids and mixtures thereof. The gamma-carboxyl group of these basic amino acids are very reactive to primary alcohols and relatively reactive to secondary alcohols.

In accordance with the present invention, a controlled esterification is carried out in order to produce the monoesters that are desired. The object is to prepare a monoester; i.e., to esterify only one of the carboxy groups and have available for further reaction amino and carboxyl functional groups.

The partial esterification of the existing hydroxyl groups on the HEMA is implemented utilizing any conventional acidic ion-exchange resin in the absence or presence of a solvent such as dioxane, acetonitrile, tetahydrofuran (THF), crown ethers, or mixtures thereof. The reaction is carried out at room temperature, preferably with stirring, until the reaction is complete, about 60 minutes. The optimum time for any given set of reactants and reaction conditions can be readily determined by routine experimentation, typically by noting the conditions giving the most rapid consumption of the amino acid powder. Aspartic acid is a white powder which "stand out" against the gold color of the acidic ion-exchange resin.

The half esters are formed by simply utilizing the stoichiometry of the HEMA and amino acid required to give the half ester. Thus, when HEMA and aspartic acid are reacted, 4 moles of HEMA are utilized for 1 mole of aspartic acid. Only 1 mole of the HEMA is required to form the half-ester, with the excess HEMA being used to plasticize the final mixture as noted later herein.

As previously noted, the reaction can be carried out with or without solvent and if a solvent is used it is preferred to use an amount equivalent to 50% of the volume of the HEMA.

As to the acidic ion exchange resin it is preferred to use an AMBERLITE resin of the weak acid type such as IR-118H. There is no criticality to the amount of ion exchange resin utilized and utilizing an amount equal in volume to the volume of HEMA is satisfactory.

The resultant half ester of the dibasic acid, is then separated from the solvent, if used, by any of the known processing methods such as evaporation, vacuum distillation, and the like after removal of the resin catalyst by decanting or filtration.

After the monoester is prepared, the amino groups can be cyclicized into N-carboxyl anhydrides (NCA). Such cyclization is well-known and phosgene is conventionally used to effect the cyclization.

The resultant monoester or cyclicized monoester is preferably combined with the bis-GMA and the usual fillers and reinforcing agents approved for use to produce a composition suitable for use as a dental filling and which will be resistant to abrasion and oral environmental attack. Examples are Bioglass, tantalum oxide nanoclusters, and the like which can also contribute to X-ray opacity. It will be understood that the composition can be used for adhesive purposes.

As to proportions of bis-GAA and HEMA monoester of amino acids used to form the dental repair composition, it is preferred to use 1 part by weight of the HEMA ester for each 1 to 10 parts by weight of the bis-GAA. If a cyclicized ester is used, it is preferred to use a 1:10 ratio of cyclicized to uncyclicized. The proportions of the other components are discussed below.

To form the dental composition for use, the bis-GAA and uncyclicized or cyclicized HEMA ester, with the other components are admixed just prior to use, applied to the tooth or teeth, and polymerized. As the bis-GAA and cyclicized HEMA ester react to cross-link, the NCA component of the HEMA ester is opened and $CO_2$ released. This released $CO_2$ acts to form microbubbles in the mass as it cures, which microbubbles by their expansive action counteract any shrinkage of the mass. Thus, the acrylic copolymerization and NCA reaction are coordinated so the $CO_2$ released can be effective in preventing shrinkage.

The copolymerization is preferably a light activated one, suitably by UV activation in which conventionally known peroxide curing agents, such as cumene hydroperoxide are utilized.

In use, the dentist or dental technician simply admixes the acrylic reactants and other components, the mixture is placed in the tooth, and ultra-violet light used to activate and effect the polymerization (cure). In short, a UV activated, peroxide initiated, addition polymerization is effected.

It is believed that since there are still carboxyl groups present that there will be no need for any of the traditional acidic cleaning of enamel or dentin as is presently done prior to using the instant composition. It is believed that the amino groups also present will aid in adhesion, even if no acidic cleaning is utilized.

As to the fillers added to the composition there can be used reinforcing fillers such as Bioglass (a calcium-phosphate silicate) and fillers such as silica, corundum, tantalum oxide, and tantalum oxide nanoclusters, or mixtures of the foregoing. For each 100% by volume of the bis-GMA/HEMA partial ester mixture there can be added from about 50 to 85% by volume of such fillers.

Optimally, to help prevent cracks in any filling over time, milled fibers such as quartz fibers, corundum fibers, silicon carbide, or silicon nitride fibers or whiskers can be incorporated as part of the composition in an amount of about 0.1 to 2% by volume for each 100% by volume of the bis-GMA/HEMA partial ester.

To help plasticize the mixture, it is also desirable to add neat HEMA which acts to prevent the mixture from becoming too viscous. Other acrylates and methacrylates, such as hydroxyethylacrylate, isopropylidene bis [2, (3)-hydroxy-3 (2)-(4-phenoxy) propyl methacrylate, decamethyl dimethacrylate, ethylhexyl acrylate-bis GMA comonomer. Mixtures thereof, and the like approved for human use can also be used. They are added in amounts required to assure flow of the composition into tooth crevices to provide most suitable fillings, the amount used can be as low as 1 to 2%, based on the total weight of the composition with the optimum amount for any given composition being determined by routine experimentation.

It will be understood that in addition to dental usage, the instant composition can also be used as a bone cement.

The invention will be further described in connection with the following examples which are set forth for purposes of illustration only.

EXAMPLE 1

4 moles of HEMA were admixed with 1 mole of 1-aspartic acid in the presence of AMBERLITE IR-118H and the mixture maintained at room temperature with stirring until the reaction was completed, about 60 minutes. The amount of AMBERLITE used was equal in volume to the amount of HEMA.

After the reaction was completed, the resultant half-esters were separated from the AMBERLITE by filtration. The yield was 100%.

EXAMPLE 2

The process of Example 1 is followed except that 1 mole of 1-glutamic acid is substituted for the 1-aspartic acid. An equally suitable monoester is obtained at room temperature conditions.

EXAMPLES 3 AND 4

The processes of examples 1 and 2 are followed except that 2.0 moles of HEEA (hydroxethyl ethacrylate) is substituted in each Example for the HEMA. In each case suitable partial esters are obtained.

EXAMPLE 5

The partial ester of Example 1 is phosgenated to cyclicize the amino acid groups into N-carboxyl anhydrides, using a conventional phosgenation process.

Namely, the partial ester is first purged with $N_2$ and then with phosgene at room temperature. The solution is then heated at 40–60° C. and purged with $N_2$ to remove HCl and the cyclicized product recovered.

EXAMPLE 6

An ester prepared in accord with Example 1 and a commercial dentin adhesive (ART Bond®, Coltene Ag, Switzerland) were compared by utilizing the same on teeth.

More particularly, one group of teeth was treated with a primer, malic acid and polymalic acid in sodium fluoride and water, made by ART Bond. Then a 12% aspartic HEMA/half ester prepared in accordance with Example 1 using the proper molar ratios of HEMA and 1-aspartic acid was applied thereover as an adhesive.

A second group of teeth was primed as set forth above, but ART Bond® adhesive was utilized in place of the 12% aspartic HEMA/half ester.

The strength of the bond of the adhesives to human tooth dentin was then measured.

It was found that the bond strength of the adhesives of the present invention averaged 15.17 MPa (mega pascales) while the prior art dentin adhesive averaged 9.06 MPa.

EXAMPLE 7

The processes of Examples 3 and 4 are followed except that allyl alcohol is substituted for the HEMA used therein. In each case more stable partial esters are obtained which are also capable of co-polymerization with bis-GMA.

While the invention has been described in connection with a preferred embodiment, it is not intended to limit the scope of the invention to the particular form set forth, but on the contrary, it is intended to cover such alternatives, modification, and equivalents as may be included within the spirit and scope of the invention as defined by the appended claims.

What is claimed is:

1. A method of making a monoester of a dibasic amino acid comprising reacting a dibasic amino acid with a hydroxyl functional acrylic compound at ambient temperature in the presence of an acidic ion-exchange resin for a time sufficient to form the half ester.

2. The method of claim 1 wherein said dibasic amino acid and hydroxyl functional acrylic compound are used in the stoichiometric amount calculated to form the monoester.

3. The method of claim 2 wherein said dibasic amino acid is aspartic acid, glutamic acid, or mixtures thereof and said hydroxyl functional acrylic is a hydroxy $C_1$–$C_4$ allyl—acrylate or methacrylate.

4. The method of claim 3 wherein the dibasic amino acid is aspartic acid and the acrylic is 2-hydroxyethyl methacrylate.

5. The method of claim 4 wherein for each mole of aspartic acid there are utilized four moles of the 2-hydroxyethyl methacrylate.

6. The method of claim 5 wherein the reaction is carried out with stirring.

7. The method of claim 6 including separating the monoester from the reaction mixture and cyclizing the amino groups thereof into N-carboxyl anhydrides.

8. The method of claim 7 wherein cyclization is effected by reacting the monoester with phosgene.

9. A composition for use in repair of teeth, comprising a dibasic amino acid partially esterfied with a hydroxyl functional acrylic compound.

10. The composition of claim 9 wherein said partial ester is a monoester.

11. The composition of claim 10 including, for each part by weight of said partial ester, from 1 to 10 parts by weight of said hydroxyl functional acrylic compound.

12. The composition of claim 11 wherein the dibasic amino acid is aspartic acid, glutamic acid, or mixtures thereof and the hydroxyl functional acrylic compound is a $C_1$–$C_4$ allyl, acrylate, or methacrylate.

13. The composition of claim 12 wherein the dibasic amino acid is aspartic acid and the hydroxyl functional compound is 2-hydroxylthyl methacrylate.

14. The composition of claim 13 including, for each party by weight of said partial ester, from 1 to 10 parts by weight of a bis-glycidylalkylacrylate.

15. The method of tooth repair comprising applying the composition of claim 9 to an area of the tooth requiring repair and curing said composition.

16. The method of claim 15 wherein the partial ester is a monoester.

17. The method of claim 16 wherein the composition includes, for each part by weight of said partial ester, from 1 to 10 parts by weight of said hydroxyl functional acrylic compound.

18. The method of claim 17 wherein the dibasic amino acid is aspartic acid, glutamic acid, or mixtures thereof and the hydroxyl functional acrylic compound is a $C_1$–$C_4$ allyl, acrylate, or methacrylate.

19. The method of claim 18 wherein the dibasic amino acid is aspartic acid and the hydroxyl functional compound is 2-hydroxyethyl methacrylate.

20. The method of claim 19 wherein a peroxide initiator is included in the composition and the composition is cured by UV activation.

* * * * *